United States Patent
Hachadorian et al.

(10) Patent No.: US 12,029,922 B2
(45) Date of Patent: Jul. 9, 2024

(54) X-RAY CT-OR MRI-BASED QUANTITATIVE CORRECTION OF CHERENKOV LIGHT EMISSION IN RADIATION DOSE IMAGING

(71) Applicant: THE TRUSTEES OF DARTMOUTH COLLEGE, Hanover, NH (US)

(72) Inventors: Rachael Hachadorian, Norwich, VT (US); Brian Pogue, Hanover, NH (US); Petr Bruza, Lebanon, NH (US); Lesley Jarvis, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 17/627,633

(22) PCT Filed: Jul. 15, 2020

(86) PCT No.: PCT/US2020/042047
§ 371 (c)(1),
(2) Date: Jan. 14, 2022

(87) PCT Pub. No.: WO2021/011600
PCT Pub. Date: Jan. 21, 2021

(65) Prior Publication Data
US 2022/0257982 A1    Aug. 18, 2022

Related U.S. Application Data

(60) Provisional application No. 62/874,124, filed on Jul. 15, 2019.

(51) Int. Cl.
*A61N 5/10* (2006.01)
*G01T 1/22* (2006.01)
*G01T 1/29* (2006.01)

(52) U.S. Cl.
CPC ........... *A61N 5/1071* (2013.01); *A61N 5/10* (2013.01); *A61N 5/103* (2013.01); *A61N 5/1039* (2013.01);
(Continued)

(58) Field of Classification Search
CPC ........ A61N 5/10; A61N 5/103; A61N 5/1039; A61N 5/1048; A61N 5/1049;
(Continued)

(56) References Cited

U.S. PATENT DOCUMENTS

| | | | |
|---|---|---|---|
| 3,718,818 A * | 2/1973 | von Arx | G01T 1/22 250/361 R |
| 9,047,659 B2 * | 6/2015 | Klose | A61B 5/0073 |
| 9,322,927 B2 * | 4/2016 | Lee | G01T 1/02 |
| 9,731,150 B2 * | 8/2017 | Hale | A61B 5/0071 |

(Continued)

FOREIGN PATENT DOCUMENTS

EP    3279669 A1    2/2018

OTHER PUBLICATIONS

International Patent Application No. PCT/US2020/042047, International Search Report and Written Opinion dated Nov. 17, 2020, 8 pages.

(Continued)

*Primary Examiner* — Allen C. Ho
(74) *Attorney, Agent, or Firm* — Cozen O'Connor

(57) ABSTRACT

A system for monitoring radiation treatment images Cherenkov emissions from tissue of a subject. A processor of the system determines densities of a surface layer of the subject from 3D images of the tissue to determine correction factors. The processor uses these factors to correct the Cherenkov images for attenuation of Cherenkov light by tissue, making them proportional to radiation dose. In embodiments, the system obtains reflectance images of the subject, determines (Continued)

second correction factors therefrom, and applies the second correction factors to the Cherenkov emissions images. In embodiments, the corrected images of Cherenkov emissions are compared to dose maps of a treatment plan. A method of correcting Cherenkov emissions images includes determining tissue characteristics from CT or MRI images in a surface volume where Cherenkov is expected, using; imaging Cherenkov emissions; and using the tissue characteristics to correct the images for variations in Cherenkov light propagation through the tissue.

20 Claims, 6 Drawing Sheets

(52) U.S. Cl.
CPC ......... *A61N 5/1048* (2013.01); *A61N 5/1049* (2013.01); *G01T 1/22* (2013.01); *G01T 1/2992* (2013.01); *A61N 2005/1055* (2013.01); *A61N 2005/1059* (2013.01); *A61N 2005/1061* (2013.01); *A61N 2005/1087* (2013.01); *A61N 2005/1089* (2013.01)

(58) Field of Classification Search
CPC .... A61N 2005/1055; A61N 2005/1059; A61N 2005/1061; A61N 5/1071; A61N 2005/1087; A61N 2005/1089; G01T 1/22; G01T 1/2992
USPC ................................ 378/62, 63, 65; 250/393
See application file for complete search history.

(56) References Cited

U.S. PATENT DOCUMENTS

| | | | |
|---|---|---|---|
| 10,201,718 B2* | 2/2019 | Pogue | A61N 5/1065 |
| 10,274,610 B2* | 4/2019 | Nelson | G01T 1/2002 |
| 10,363,009 B2* | 7/2019 | Requardt | G06T 7/0012 |
| 10,365,383 B2* | 7/2019 | Nelson | A61B 6/037 |
| 10,509,135 B2* | 12/2019 | Nelson | A61B 6/032 |
| 10,940,332 B2* | 3/2021 | Zhang | A61N 5/1071 |
| 11,000,703 B2* | 5/2021 | Krishnaswamy | A61B 5/0071 |
| 11,235,177 B2* | 2/2022 | Krishnaswamy | A61N 5/1075 |
| 11,400,315 B2* | 8/2022 | Ueno | G01T 1/2002 |
| 11,633,627 B2* | 4/2023 | Krishnaswamy | G01T 1/023 378/65 |
| 2013/0108132 A1 | 5/2013 | Klose | |
| 2016/0263402 A1 | 9/2016 | Zhang et al. | |
| 2017/0304653 A1 | 10/2017 | Hale et al. | |
| 2018/0085080 A1 | 3/2018 | Requardt et al. | |

OTHER PUBLICATIONS

Hachadorian et al., Correcting Cherenkov images for large-scale tissue-optical property attenuation using SFDI and patterned light reflectance for quantitative dosimetry, Proceedings of SPIE vol. 10874, 2019, 10 pages.
Ren et al., Robust Estimation of Electron Density From Anatomic Magnetic Resonance Imaging of the Brain Using a Unifying Multi-Atlas Approach, International Journal of Radiation Oncology, Biology, Physics., 97(4), Mar. 15, 2017, 17 pages.
European Patent Application No. 20840220.6 extended European search report dated Jul. 31, 2023, 8 pages.

* cited by examiner

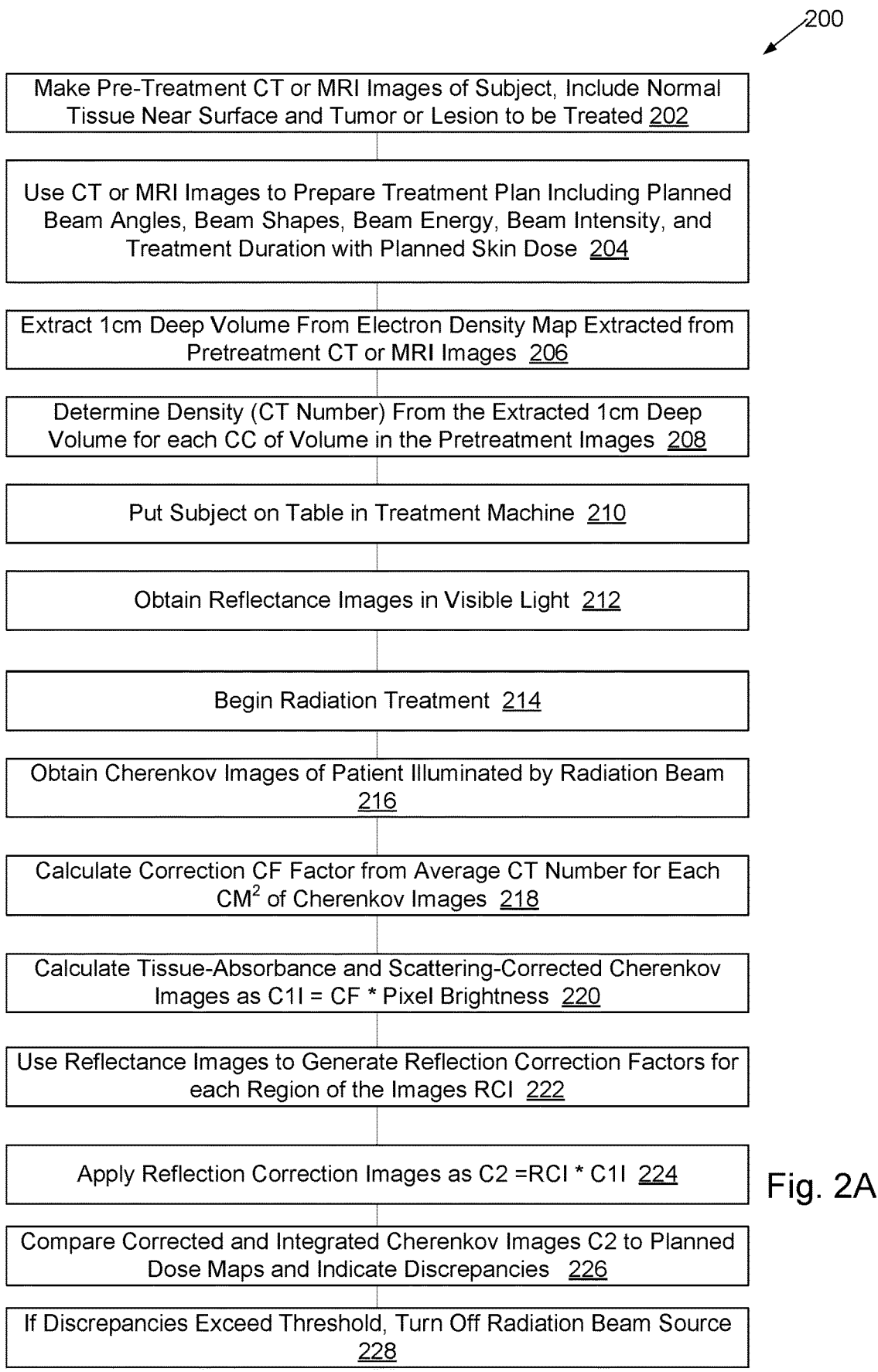

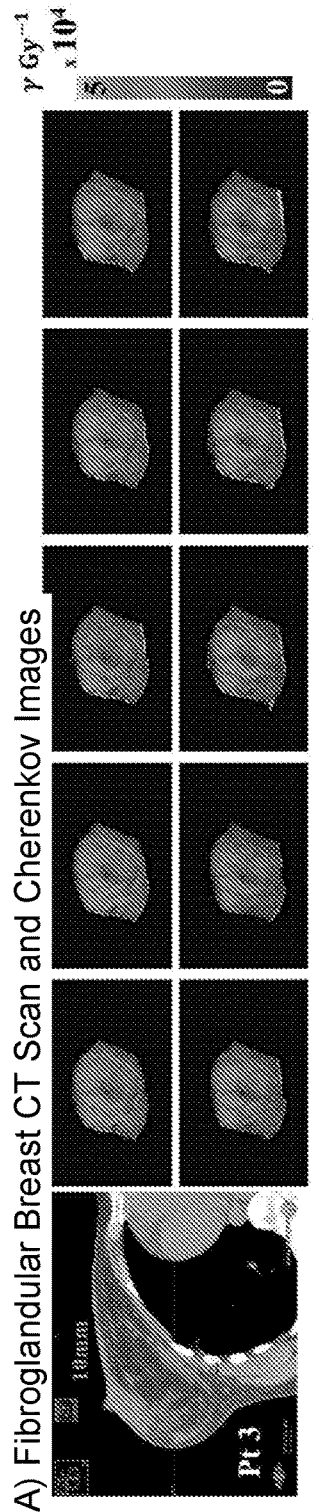
Fig. 3(A) Fibroglandular Breast CT Scan and Cherenkov Images
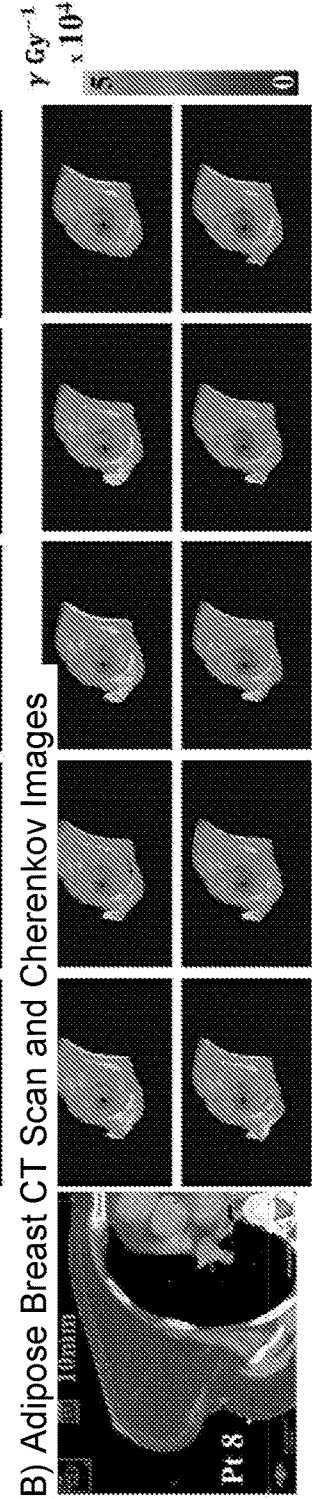
Fig. 3(B) Adipose Breast CT Scan and Cherenkov Images
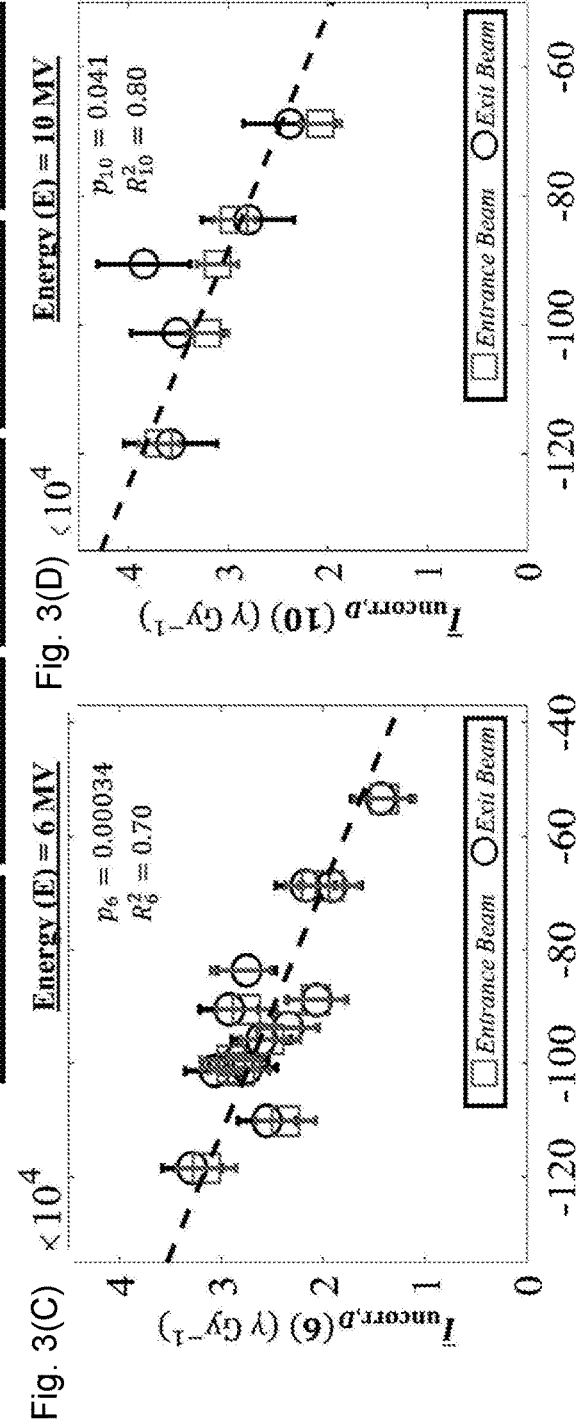
Fig. 3(C)
Fig. 3(D)

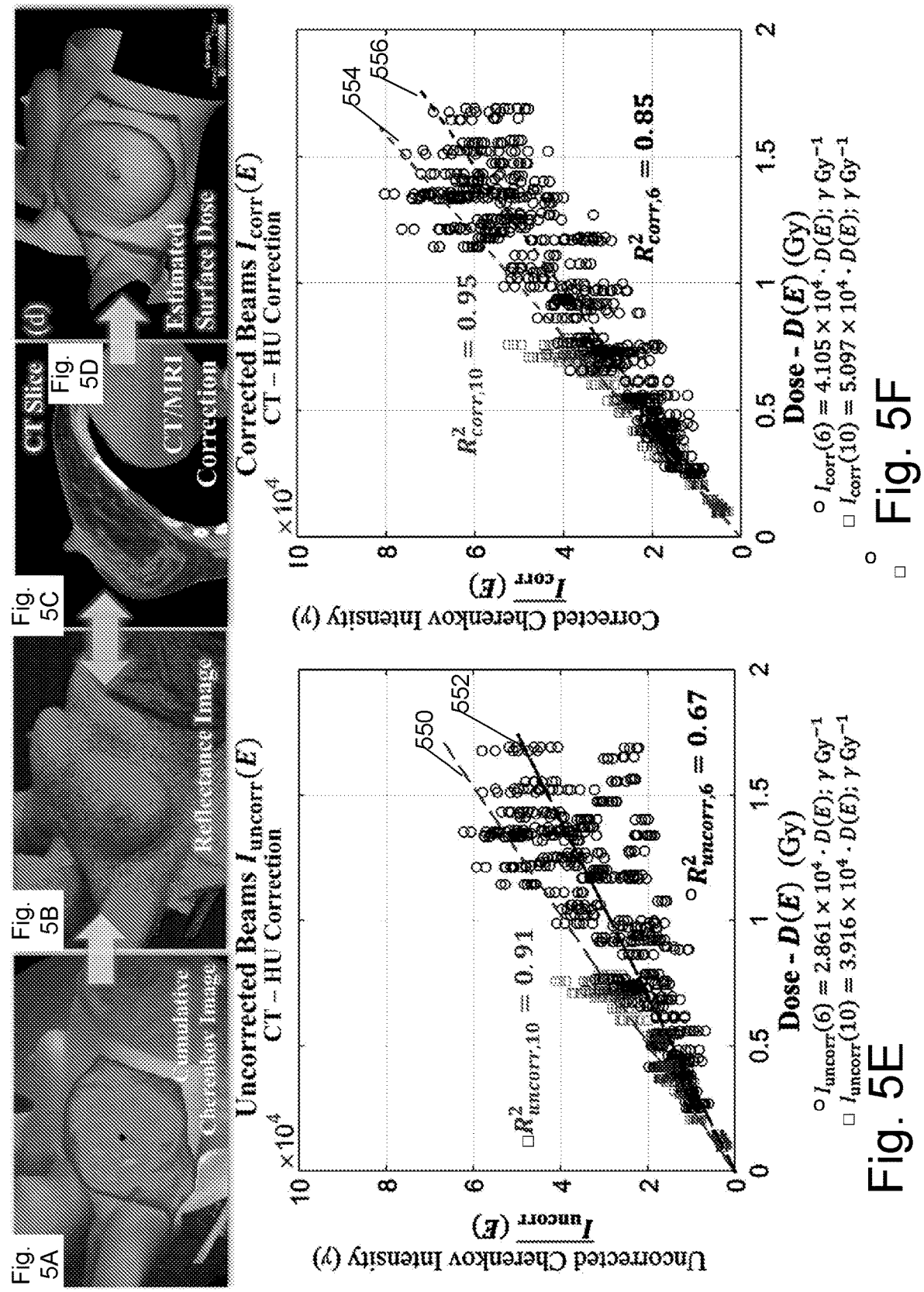

X-RAY CT-OR MRI-BASED QUANTITATIVE CORRECTION OF CHERENKOV LIGHT EMISSION IN RADIATION DOSE IMAGING

CROSS-REFERENCE TO RELATED APPLICATION

The present application is a 35 U.S.C. § 371 filing of International Application No. PCT/US2020/042047 filed 15 Jul. 2020, which claims priority to U.S. Provisional Patent Application 62/874,124 filed 15 Jul. 2019. The entire contents of provisional patent application 62/874,124 is incorporated herein by reference.

GOVERNMENT RIGHTS

This invention was made with government support under grant nos. R01 EB023909 and R44 CA232879 awarded by the National Institutes of Health. The government has certain rights in the invention.

BACKGROUND

Imaging Cherenkov emission during radiation therapy cancer treatments can provide a realtime, non-contact sampling of the entire dose field. The Cherenkov signal emitted from tissue is proportional to deposited dose, however, it is affected by attenuation from optical properties intrinsic to tissue of the patient. For example, when treating breast tumors, the Cherenkov signal as captured by an external camera is affected by whether the breast is composed primarily of adipose, fibroglandular or muscle tissues, as well as layers of skin with pigmentation in them.

SUMMARY

A system for monitoring radiation treatment images Cherenkov emissions from the tissue of a subject, a source of volumetric images of the tissue composition and layers, and a processor configured to determine optical attenuation of the surface layers of the subject from these volumetric images and determines correction factors therefrom. The processor applies the correction factors to the images of Cherenkov emissions. In embodiments, the system also obtains reflectance images of the subject, determines second correction factors therefrom, and applies the second correction factors to the images of Cherenkov emissions. In embodiments, the corrected images of Cherenkov emissions are compared to dose maps of a treatment plan. A method of generating corrected images of Cherenkov emissions includes determining calibrated tissue properties such as electron density in a tissue surface volume from CT images or specifying tissue classification from Magnetic Resonance Images (MRI) based upon the soft tissue differences in the image; imaging Cherenkov emissions from the tissue; and using the electron density or tissue type classification in the tissue surface volume regions where Cherenkov is emitted from, to correct the images of Cherenkov generated for the tissue specific attenuation. These calibrated images of Cherenkov emission are then reported as a surrogate measure of the radiation dose deposited in these surface tissue volumes.

BRIEF DESCRIPTION OF THE FIGURES

FIG. 2A is a flowchart of patient treatment, imaging, and image correction in an embodiment based on electron density mapping.

FIG. 3(A) illustrates scans of one patient's CT scan showing dense, fibroglandular tissue in most of the breast; adjacent are Cherenkov images from sequential fractions, normalized with respect to the prescribed breast surface dose from the treatment plan, shown as an intensity map in Cherenkov photons imaged per centigray (cGy).

FIG. 3(B) illustrates scans of one patient's CT scan showing primarily adipose tissue in most of the breast; adjacent are Cherenkov images from sequential fractions, normalized with respect to the prescribed breast surface dose from the treatment plan, shown as an intensity map in Cherenkov photons imaged per cGy.

FIG. 3(C) is a chart of electron density in Hounsfield units (HU) versus observed, uncorrected, Cherenkov image brightness for 6 MV X-ray beams.

FIG. 3(D) is a chart of uncorrected tissue electron density in Hounsfield units (HU) versus observed Cherenkov image brightness for 10 MV X-ray beams.

FIG. 5A illustrates a Cherenkov image integrated over an entire treatment session and corrected for tissue density but not reflectance.

FIG. 5B is a CT slice showing that the breast imaged in FIG. 5A has significant fibrocystic character.

FIG. 5C illustrates a reflectance image of the breast imaged in FIG. 5A.

FIG. 5D illustrates actual radiation dose administered to the breast imaged in FIG. 5A as determined from Cherenkov images of the breast during treatment and corrected for both tissue density and reflectance.

FIG. 5E illustrates Cherenkov light versus administered radiation dose for 6 MV and 10 MV beams without correction as described herein FIG. 5F illustrates corrected Cherenkov light versus administered radiation dose for 6 MV and 10 MV.

DETAILED DESCRIPTION

Cherenkov emission can be imaged from in-vivo patient tissue in real time, and has illustrated a general proportionality with absorbed dose. However, the light attenuation from blood, melanin and endogenous scatterers in tissue alter the emitted intensity, making imaging of Cherenkov from different patients not directly proportional to the deposited dose, and thereby limiting quantitative accuracy. A critical step toward making emitted Cherenkov light—electromagnetic radiation including visible light emitted when charged particles exceed the speed of light in the medium through which they are passing—a direct surrogate for absorbed dose is to correct for observed tissue optical property variations between patients and treatment sites.

Figure 1:
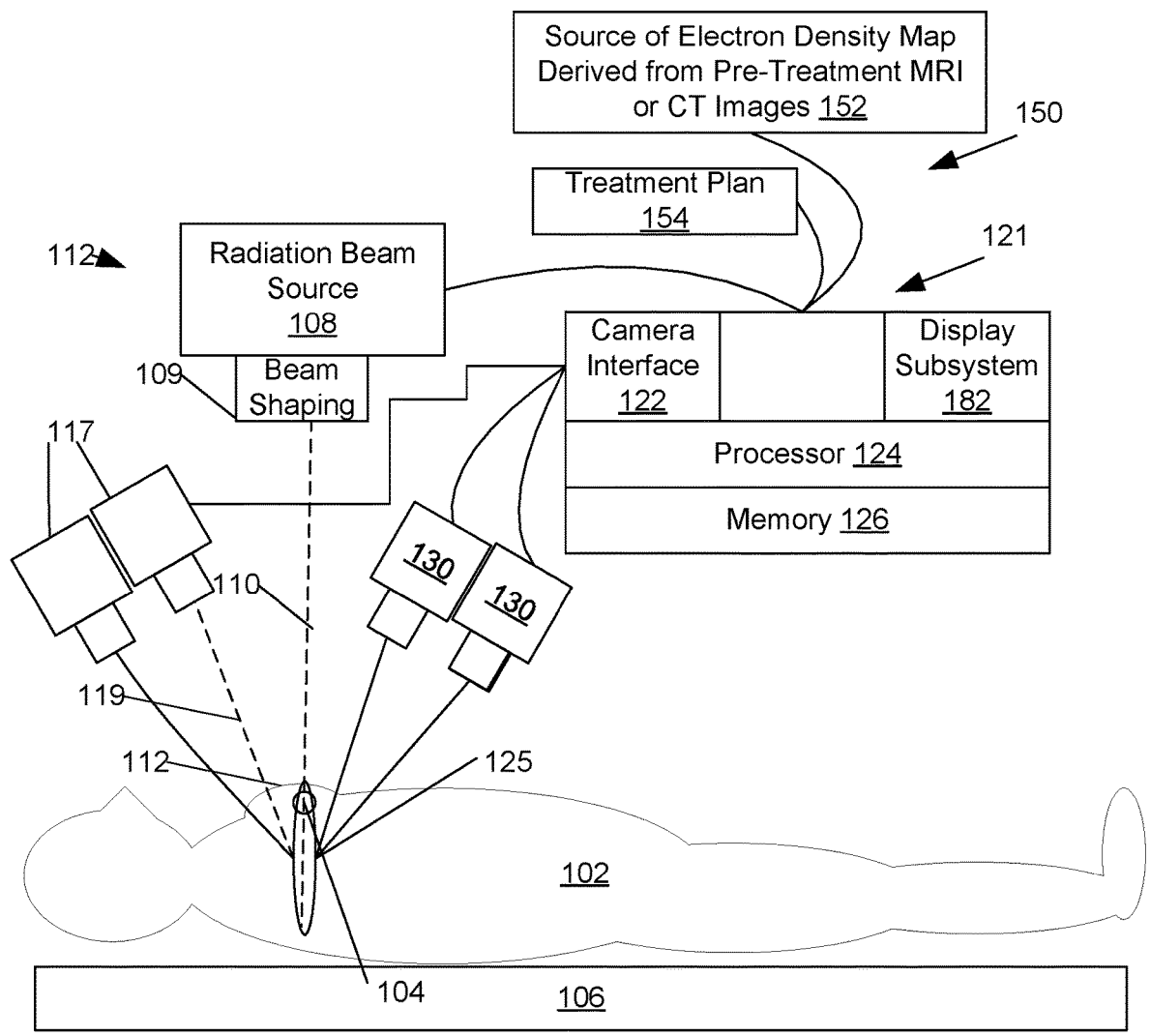
FIG. 1 is a schematic diagram of a system for treating a tumor in a subject.

A system 150 for providing radiotherapy and monitoring factors known to affect the effectiveness of radiotherapy, and monitoring effects of radiotherapy on tissue, is illustrated in FIG. 1.

A subject 102 containing a tumor 104 requiring radiotherapy is placed on a treatment table 106 with padding (not shown) and positioned to receive a shaped, pulsed, treatment beam 110 through normal tissue to tumor 104 from an accelerator 108 through beam shaper 109, or other device for providing high energy radiation. The system herein described uses incident radiation from accelerator 108 at beam energies of at least 200 keV because, at beam energies of less than 200 keV (0.2 MeV), Cherenkov radiation is typically of insufficient intensity for imaging. In a particular embodiment, the accelerator 108 provides a beam of electrons having energy of 6 million electron volts (6 MeV) or greater, in a particular embodiment the beam energy lies between 6 and 24 MeV. In an alternative embodiment, the device for providing high energy radiation provides a beam of high energy photons, the photons interact with tissue or tumor to produce charged particles that in turn produce Cherenkov radiation. In an alternative embodiment, the accelerator 108 provides a high-energy proton beam. In an alternative embodiment, the radiation source is implanted in the body, inducing Cherenkov emission light directly as charged particles are emitted during radiation decay.

Since high radiation doses are desired in tumors, while high doses are not desired in surrounding normal tissue or on skin because those tissues can be damaged by radiation, provisions are typically made for varying arriving beam delivery angles by, for example, rotating the subject 102 in the beam, rotating the radiation source about the subject, or periodically interrupting treatment to reposition the subject. Additionally, the beam is shaped in a collimator either into a static beam, or in other embodiments the beam shape is dynamically changed while beam angles are changed, to allow dose delivery customized to the shape of the tumor to be treated at each delivered beam angles.

A camera system having one or more cameras 117, each having a lens system and an array photosensor for imaging, is positioned some distance from the subject and is used to image Cherenkov light emitted from the tissue. Camera system 117 is positioned out of the radiation beam 110 to avoid damage to the camera system that may be caused by radiation beam 110, while being aimed and positioned to image Cherenkov light 119 emitted from an interaction zone 125 where interactions of the radiation beam 110 takes place with the subject 102—we note the beam may penetrate deeper in the subject than tumor 104 and may interact with normal tissue 112 as well as tumor 104 tissue of the subject 102. In some embodiments, cameras 117 incorporate image intensifiers and are thus capable of responding to very low levels of Cherenkov light emitted by the tissue during treatment. Cameras 117 are coupled to provide images through a camera interface 122 to a processor 124 of an image processing system 121.

Processor 124 analyzes images from camera 117 to provide indications of skin dose and map deeper radiation dose provided by beam 110 to normal 112 and tumor 104 tissue of the subject. In embodiments, one or more stereo pairs of cameras 130 are also provided. Images captured by the stereo pairs of cameras 130 are processed by processor 124 to generate a map of a surface of the subject 102.

As beam 110 interacts with tissue of the subject in interaction zone 125, the beam causes Cherenkov light to be emitted because either charged particles of the beam exceed the effective speed of light in the tissue, or photons of the beam interacting with tissue generate charged particles having speed greater than the effective speed of light in the tissue.

The Cherenkov light propagates from the tissue in the interaction zone through skin and is imaged by cameras 117 to generate Cherenkov images. The processor 124 of image processing system 121 synchronizes capture of the Cherenkov images to pulses of the treatment beam 110 and receives the Cherenkov images. Once received, the processor 124 improves the Cherenkov images by techniques such as image averaging, subtraction of averaged background, and similar techniques.

As Cherenkov light propagates from locations in tissue where it is generated by interaction with tissue, the Cherenkov light is subject to scattering and absorption by the tissue as well as blood within the tissue, and is further subject to absorption by melanin and other pigments in the skin it must penetrate on leaving the subject; only once it leaves the subject can it be imaged.

We have determined that improved images of Cherenkov light emitted from tissue of a subject can be generated if the images are corrected for this scattering and absorption of that light in tissue and skin of the subject. To correct Cherenkov light images for scattering and absorption in tissue and skin, it is necessary to determine correction factors that compensate for absorption and scattering parameters for that tissue and skin.

To provide data for correction of the Cherenkov images, and to permit comparison of actual to planned treatment, pre-treatment magnetic resonance imaging (MRI) or computed X-Ray tomography CT images are prepared of the subject, these images are used to prepare a treatment plan 154 as known in the art. If MRI images are used, an electron density map is prepared from the MRI images using a method such as that described in *Robust Estimation of Electron Density from Anatomic Magnetic Resonance Imaging of the Brain Using a Unifying Multi-Atlas Approach*, Shangjie Ren et al., Int J Radiat Oncol Biol Phys. 2017 Mar. 15; 97(4): 849-857. Alternatively, if CT images are available, the CT images directly provide an electron density map. The electron density map 152 and a treatment plan 154 are imported into memory of the image processing system 121 from a source of images and a source of the treatment plan.

To obtain corrected images of Cherenkov light emitted from a subject, the processor of the system is operated according to the method 200 illustrated in the flowchart of FIG. 2. This method begins with making either an electron density map derived from pretreatment MRI images, or making pretreatment computed X-ray tomography (CT) images 202 of the tumor or other lesion to be treated with surrounding tissues, these images typically portray a three-dimensional voxel-based model of the lesion and surrounding tissues. Imaging of this type is often done when cancers, such as breast cancer, are diagnosed so the pretreatment images can be used to confirm diagnosis and stage of the disease. As is common in the art, the pretreatment images are then used for treatment planning; in the event radiotherapy of the lesion is anticipated the images are used to determine a radiotherapy treatment plan 204 that typically includes energies, directions, intensities, and shapes of radiation beams to be used during therapy, as well as duration of each treatment session and a number of treatment sessions.

Before radiotherapy treatment begins, pretreatment MRI images are processed to make an electron density map that may be substituted for CT images; either the electron density map or pretreatment CT images are processed by image processing system 121 to extract 206 and determine densities 208 of a surface layer, in an embodiment the surface layer is a 1 centimeter (cm) deep layer of the subject's surface; these densities may be determined in Hounsfield units (HU) as known in the art of CT image processing and electron density maps. The subject is then positioned 210 on a table in a radiotherapy system such that a radiation beam generated by a radiation source 108 of the system—typically a linear accelerator or cyclotron—can reach the lesion, the surface of the subject is imaged 212 in reflected visible light by cameras 117 to obtain information of skin coloration useful for adjustment of captured Cherenkov images. Note that these reflectance images may also be obtained or updated during radiation treatment between pulses of the radiation beam.

In an alternative embodiment, CT or MRI imaging is updated between sessions of radiotherapy treatment, the updated images are processed into an electron density map and extracted to determine updated densities of the 1-centimeter deep layer of the subject's surface as previously described. The updated densities replace pretreatment densities for correction of Cherenkov images in subsequent treatment sessions.

The measurement of tissue electron density or CT number, also known as the Hounsfield number HU, is extracted from pretreatment images 152. We have found that this CT number can be used to estimate absorption and scattering parameters of Cherenkov emissions for the tissue, and these estimated absorption and scattering parameters can then be used to correct images of Cherenkov emission intensity for scattering and absorption of Cherenkov emissions in the type of tissue being treated. Most patients receive pre-simulated treatment and will have received pretreatment imaging of their tissue that is used for generating the treatment plan 154. From this pretreatment imaging, we therefore extract and evaluate CT numbers for the volumes of the patient that are irradiated, and therefore the regions from which the Cherenkov light is being emitted. Using this extracted volume and CT numbers, we then normalize the Cherenkov light intensity either globally or regionally in captured Cherenkov images.

In an embodiment for use in radiation treatment of the breast, a mean CT number is calculated using a contour created within the Eclipse treatment planning software from body contours of the subject including tissue between a surface of the subject to 10 mm below the surface of the subject; this 10 mm depth being an estimate of a maximum depth in the subject that Cherenkov light is expected to be emitted and propagate to skin surface of the subject without undue absorption in tissue of the subject. The mean CT number is calculated from CT scan density for each cubic centimeter observed in this 3D structure, as illustrated from the 2D slices shown in FIG. 3 in the left panels showing the axial breast regions. depth of 10 mm was chosen to account for the maximum depths from which Cherenkov photons could reasonably originate and travel to the surface without being substantially absorbed. In FIGS. 3(c) and 3(d), measured data from these images were divided into groups according to prescribed irradiation treatments for correlation testing:

i) Entrance/RPO (squares, FIG. 3(c)) at 6 MV (n=13, p=0.00024, R2=0.76);
ii) ii) Exit/LAO (circles, FIG. 3(c)) at 6 MV (n=13, p=0.00028, R2=0.75);
iii) iii) Entrance/RPO (FIG. 3(d), squares) at 10 MV (n=4, p=0.269, R2=0.53); and
iv) iv) Exit/LAO (circles, FIG. 3(d)) at 10 MV (n=4, p=0.026, R2=0.95).

Each point shown is averaged over all fractions for one given patient, such that the fits were unbiased. (Pt30: n=5, Pt31: n=10, Pt32: n=10, Pt35: n=6, Pt36: n=6, Pt37: n=10, Pt39: n=13, Pt41: n=17, Pt 44: n=11, Pt45: n=8, Pt56: n=4, and Pt58: n=8). The Cherenkov light observed decreased with denser tissues, as shown in FIG. 3a. Correlation line slopes, m, for both entrance and exit data at 6 MV were nearly identical at −248 photons/(cGy HU) and −235 counts/(cGy HU), respectively, for fitting to the linear expression:

$$C = m*HU + k$$

The parameters m and k in the preceding equation are determined 218 as a correction factor CF for each 1 cm region of the subject's surface.

Radiation treatment begins 214 with beams of electrons, protons, X-rays, or other charged particles of sufficient energy to induce Cherenkov emission in tissue of the subject. The Cherenkov emissions from tissue escape through the subject's skin surface and are imaged 216 by a Cherenkov camera. In particular embodiments, the Cherenkov camera is an image-intensified, gated, camera that captures images of Cherenkov light during, and synchronized to, pulses of the beam while ignoring light received between pulses. In some embodiments, the Cherenkov camera also captures background light images between pulses of the beam, the images of Cherenkov light are corrected by subtracting the background light images to form raw Cherenkov images.

The raw Cherenkov images are registered to the images from which the CT numbers, and thus the correction factors CF, were derived.

For each raw Cherenkov image, C, corresponding to CT number HU. The subsurface breast tissue HU value was found to be directly correlated to the amount of Cherenkov light per unit cGy of dose (p-values<0.05), and this was true for both 6 MV beams, and one of the 10 MV exit beams. A linear correction 220 was applied to each Cherenkov/cGy value at each pixel of the raw Cherenkov images for both 6 MV and 10 MV beams based upon this, using the correction factor CF calculated above, as shown in the second and fourth columns of FIG. 4 for 6 MV exit and entrance images, and the sixth and eighth columns of FIG. 4 for 10 MV exit and entrance images, respectively, using a linear correction inverse from the fit line expressed as:

$$C_{calib,i} = \frac{C_i}{m*HU_i + k} = CF_i * C_i$$

where $C_{Calib,i}$ is the tissue-absorbance corrected, dose-normalized Cherenkov median in counts/cGy for each measurement i. These corrections equalized the data, reducing the calculated slope to −8 counts/(cGy HU) for the 6 MV entrance beam, −12 counts/(cGy HU) for the 6 MV exit (FIG. 4, $4^{th}$ column), and −28 counts/(cGy HU) for 10 MV entrance and −17 counts/(cGy HU), for 10 MV exit beams.

Figure 4:
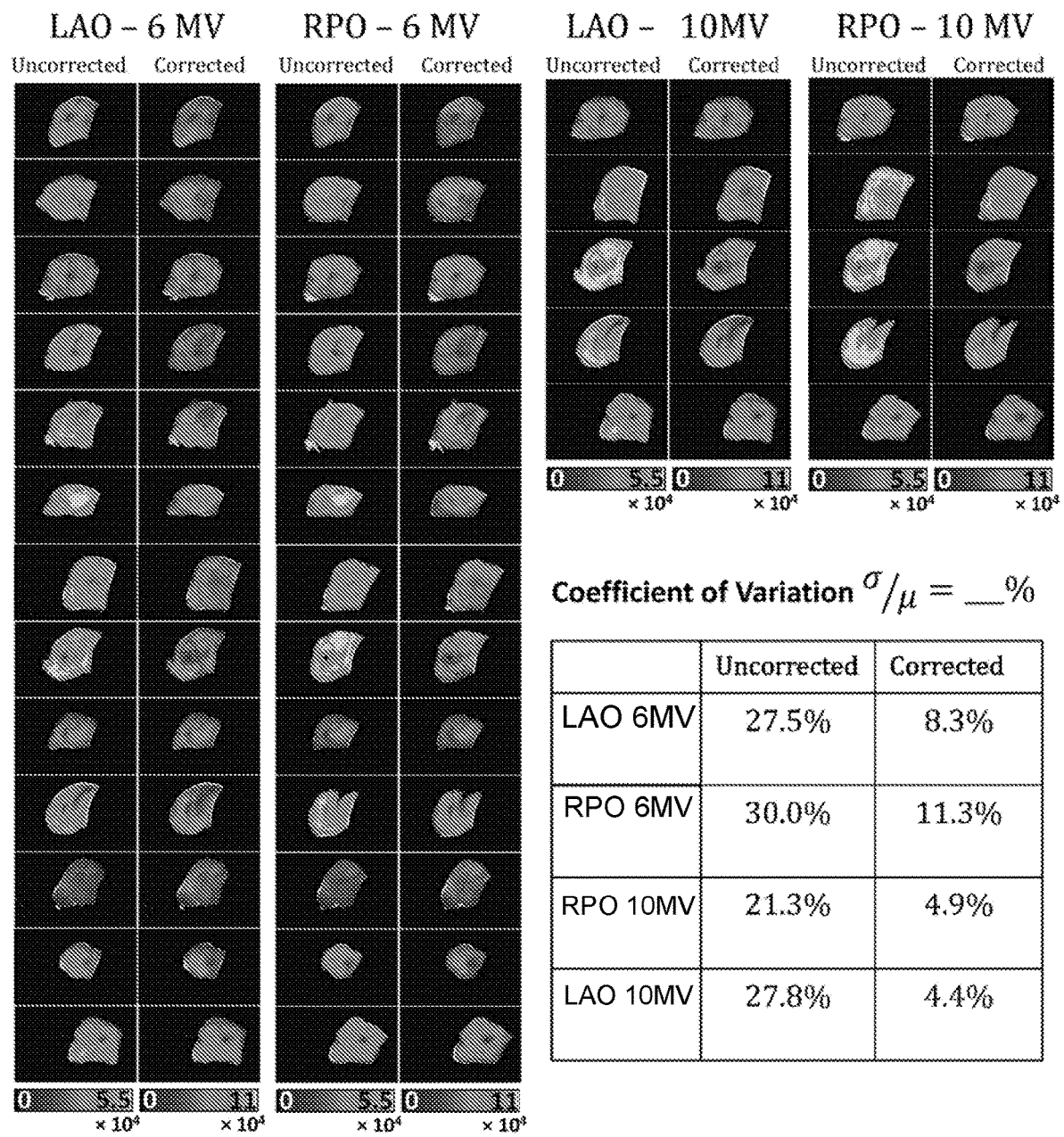
FIG. 4 illustrates observed Cherenkov light, planned surface dose, Cherenkov emissions/planned surface dose, and corrected Cherenkov images illustrating success of the correction method discussed herein.

The correction, as shown in the bottom right corner of FIG. 4, reduces the coefficient of variation from 27% for 6 MV exit beams to 8.3%, from 30% for 6 MV entrance beams to 11.3%, from 21.3% to 4.9% for 10 MV entrance beams, and from 27.8% to 4.4% for 10 MV exit beams.

These figures show corrected Cherenkov light intensities are significantly more representative of actual radiation dose administered to the patient than uncorrected Cherenkov light intensities.

Figure 2B:
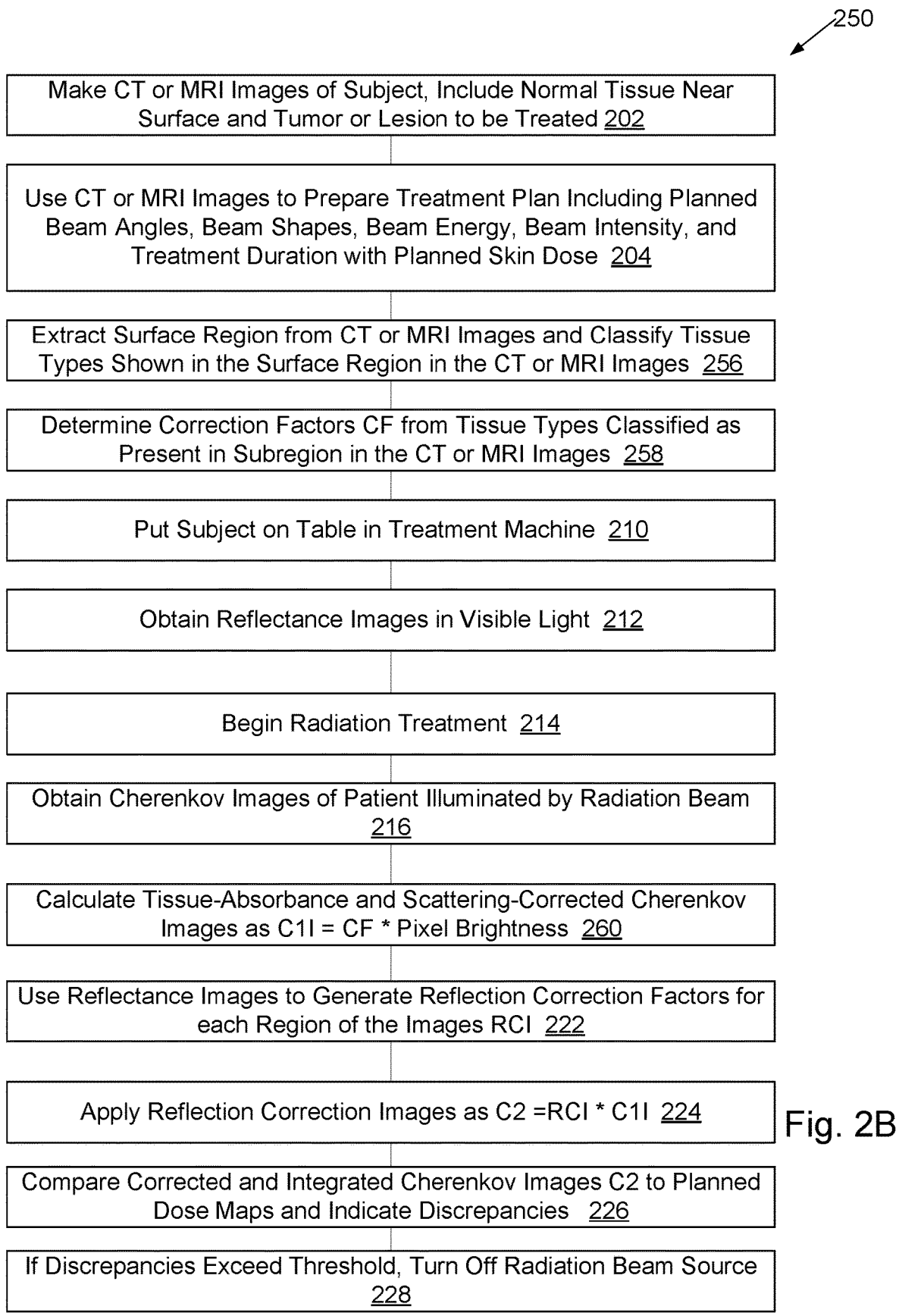
FIG. 2B is a flowchart of patient treatment, imaging, and image correction in an embodiment based on tissue classification.

In an alternative embodiment 250 (FIG. 2B), after the voxel-based three-dimensional CT or MRI images are made 202 that are used to create 204 the treatment plan, in steps equivalent to those illustrated in the embodiment 200 of FIG. 2A, tissue structures and boundaries in a surface volume of subject's tissue are extracted 256 from the images. In a particular embodiment the surface volume is one centimeter deep, since Cherenkov emissions photons from this depth can often propagate to tissue surface and be imaged. These tissue structures classified according to tissue type by a classifier that processes the images to generate a tissue type map of a surface region of the subject. For each subregion, in an embodiment a cubic centimeter, of the subject's tissue, a correction factor CF is determined 258 by looking up tissue types and tissue layers present in that subregion in a table of correction factors and tissue types. The subject is positioned for radiation treatment 210, reflectance images obtained 212, radiation treatment begun 214, and uncorrected Cherenkov images obtained 216, as with the embodiment of FIG. 2. The correction factors determined from tissue types in step 258 are used instead of correction factors determined from electron density maps to calculate 260 Cherenkov images compensated for tissue absorption and scattering of Cherenkov photons.

Before or after the Cherenkov images are corrected for tissue absorbance and scattering, the absorbance and scattering producing skin-related attenuation. As described above with reference to FIG. 2A or FIG. 2B, the Cherenkov images are also corrected for skin attenuation using reflectance images, which were taken using the Cherenkov camera under visible light illumination. The reflectance images are used to compute 222 reflection correction factors RCI for each region of the images, these are then multiplied 224 by the Cherenkov counts at each pixel of the tissue-absorbance corrected images $C_{calib,i}$. FIG. 5 illustrates results of linear correction of the Cherenkov images for quantitative dosimetry calibration, beginning with the cumulative Cherenkov images taken during treatment and by applying both an HU-based (FIG. 5*b*) correction for tissue attenuation and a reflectance correction for skin attenuation; the reflectance correction being performed through normalization of a reflectance predicted value.

The calibrated results are organized in FIG. 4, where the Exit 6 MV beam data is shown for patients 32, 41, 44, 45, 56 and 58. These Cherenkov images of the six patients were corrected using both an HU (or CT number)-based correction and a surface reflectivity correction. The column labeled "Cherenkov" shows each raw Cherenkov image recorded during radiotherapy treatment (not dose normalized, in photon units) as compared to the planned surface dose expected to be delivered in the column labeled "Planned Surface Dose" in units of cGy. Dividing the Cherenkov image by the planned surface dose yields the result in the column labeled "Cherenkov/Unit Dose Uncorrected", or the raw Cherenkov photons emitted per planned surface dose (photons/cGy). The median value of each image was taken, and averaged in the bar chart below. The coefficient of variation (COV) was used as a metric for variability across patient data sets at 23.7% for these raw or uncorrected Cherenkov images in the column labeled "Cherenkov/Unit Dose Uncorrected". After both corrections were carried out, the resulting images are shown in the column labeled "Cherenkov/Unit Dose Corrected.", with its respective COV bar chart below, showing decreased variability between patients, with COV=6.8% for the exit side 6 MV beams. For the 6 MV entrance beams, the uncorrected images had COV=25.4%, and when corrected COV=8.0%. For the 10 MV beams, the entrance beam uncorrected and corrected COV values were 17.7% and 4.6%, respectively, and finally the exit beam uncorrected and corrected COVs were 23.3% and 8.9%, respectively. Thus, the employed HU or CT-number-based corrections better equalized the data for large scale tissue optical property variations. These large-scale tissue optical property variations presumably from tissue composition variations as indicated by differences in average HU value in a surface region of the tissue.

To test the linearity of a relationship between calibrated Cherenkov light and absorbed dose, a final test of the correlation was carried out on all 108 image data sets testing multiple regions across the breast. Paired circular regions of interests (ROIs) were identified in the corrected and uncorrected Cherenkov images that avoided highly absorbing areas such as nipples and significant vasculature; we were then able to plot resulting average Cherenkov light. In FIG. 5E line 550 represents a linear fit to uncorrected Cherenkov emissions at 10 MV beam energies (shown as squares) and line 552 represents a linear fit to uncorrected Cherenkov emissions at 6 MV beam energies (shown as circles). Similarly, in FIG. 5F line 554 represents a linear fit to corrected Cherenkov emissions at 10 MV beam energies (shown as squares) and line 556 represents a linear fit to corrected Cherenkov emissions at 6 MV beam energies (shown as circles), lines 554 and 556 are corrected for both tissue density and reflectance as described herein. Lines 550-556 are all plotted against administered dose in centigrays. These show the relationships between the uncorrected and corrected Cherenkov photon counts, averaged over an unattenuated region of the image. The same ROI's were evaluated for all data sets. The linearity of the 6 MV beam increased drastically, (R2=0.73, uncorrected) and (R2=0.94, corrected), and the 10 MV entrance and exit relationships remained mostly unchanged. The result is two trends that, post correction, could lend absolute, large scale dose insight, at the time of treatment.

Thus, information provided by processing the patient CT scan is used to correct for tissue related skewing of optical light emission. Perfecting the utilization of Cherenkov light as a surrogate for absorbed dose allows clinicians to verify the quantitative accuracy of the delivered plan at the time of treatment. If a mechanical issue or treatment inconsistency between the delivered treatment and planned treatment is found, action may be taken instead of allowing the inconsistency to go unnoticed.

The technique disclosed herein allows for correction of Cherenkov images for large-scale tissue differences, and not attenuation due to small-scale, high-absorbing features such as blood vessels, moles, tattoos, and areolas in the case of breast cancers. These may be overcome by using higher-resolution systems.

Once the corrected Cherenkov images are obtained for each treatment session, they are converted and integrated, then used to determine actual applied dose maps (FIG. 5D) and compared 226 to a dose map of planned treatment for that session; the system thus monitors radiation treatment to verify that actual applied dose maps agree with planned treatment dose maps of each session.

If any significant discrepancies between planned treatment dose maps and the actual applied dose maps are seen, planned treatment dose maps and treatment plans including planned beam angles, intensities, energies, shapes, and durations of further treatment sessions are adjusted as necessary to achieve sufficient treatment of lesions being treated without overexposure of the patient, or of the patient's tissues including skin, to radiation. In a particular embodiment, the corrected Cherenkov images are converted and integrated to actual applied dose maps and these actual applied dose maps are compared to planned treatment dose maps in real time, if discrepancies between the actual applied and planned treatment dose maps exceed a threshold the treatment is aborted by the image processing system 121 sending commands to turn off 228 radiation source 108.

Combinations

The concepts herein described may be combined in various ways in real physical systems and machines. Among combinations anticipated by the inventors are:

A system designated A for monitoring radiation treatment of a subject by generating and correcting images of Cherenkov emissions from tissue of a subject including a camera adapted to create images of Cherenkov emissions from the tissue of the subject, the Cherenkov emissions produced during radiation treatment of the subject by interaction of a treatment beam with tissue of the subject; a source of three-dimensional voxel-based images of the subject's tissue, selected from the group consisting of X-ray Computed Tomography (CT) images and Magnetic Resonance Images (MRI); a processor adapted by firmware in memory to determine properties of a surface layer of tissue of the subject from the three-dimensional voxel-based images and determine optical Cherenkov correction factors CF compensating for tissue attenuation therefrom using a correction factor determination method of calculating correction factors based upon electron density in the surface layer of the subject as provided by the CT images, estimating a property map of the surface layers of the subject from the MRI images and calculating correction factors therefrom, and determining a tissue type map of the surface layer of the subject and determining correction factors for Cherenkov attenuation by tissue therefrom. The processor is also configured to apply the correction factors (CF) to the images of Cherenkov emissions from tissue of the subject to prepare Cherenkov images corrected for Cherenkov light attenuation in tissue of the subject.

A system designated AA including the system designated A wherein the surface layer is sufficiently thick to include subsurface layers of tissue from which Cherenkov is emitted from the tissue, and is at least 5 millimeters (mm) thick.

A system designated AB including the system designated A or AA wherein the correction factor determination method comprises calculating correction factors from electron density in the surface layer of the subject as provided by the CT images.

A system designated AC including the system designated A or AA wherein the correction factor determination method comprises estimating an electron density map of the surface layer of the subject from the MRI images and calculating correction factors from the electron density map.

A system designated AD including the system designated A or AA wherein the correction factor determination method comprises determining a tissue type map of the surface layer of the subject and determining correction factors from the tissue type map.

A system designated AE including the system designated AA, AB, AC, AD, or AE wherein the camera is configured to obtain reflectance images of a surface of the subject, the processor is configured to determine second correction factors (CF2) therefrom and to apply the CF2 to the images of Cherenkov emissions from tissue of the subject to generate corrected Cherenkov emissions images, the corrected Cherenkov emissions images corrected for skin attenuation of the Cherenkov emissions.

A system designated AF including the system designated A, AB, AC, AD, or AE, wherein the processor is configured to compare the corrected Cherenkov emissions images to a treatment plan of dose delivery.

A system designated AG including the system designated AF wherein the processor is configured to shut off a radiation source if the corrected Cherenkov emissions images differ from the treatment plan by more than a threshold.

A method designated B of generating corrected images of Cherenkov emissions from tissue exposed to radiation includes making X-Ray computed tomography (CT) images or Magnetic Resonance (MRI) Images of the tissue; extracting a tissue surface volume from the CT or MRI images; determining correction factors CF in the tissue surface volume from the CT or MRI images, the correction factors correcting Cherenkov emissions images for tissue absorbance; obtaining images of Cherenkov emissions from the tissue as the tissue is exposed to radiation from a radiation beam source; and using the correction factors to correct the images of Cherenkov emissions.

A method designated BA including the method designated B further comprising obtaining reflectance images of a surface of the tissue, and using the reflectance images to further correct the images of Cherenkov emissions for skin attenuation.

A method designated BB including the method designated BA or BB wherein the CT or MRI images are CT images and the correction factors are determined from CT density by calculation from CT density.

A method designated BC including the method designated B or BA wherein the CT or MRI images are MRI images and the correction factors are determined by using the MRI images to estimate an electron density map and calculation from the electron density map.

A method designated BD including the method designated B or BA wherein tissue types in the tissue surface volume are classified from the CT or MRI images to generate a tissue type map, and the correction factors are determined according to the tissue type map.

A method designated BE including the method designated B for monitoring radiation treatment includes the method designated B, BA, BB, BC, or BD to generate corrected images of Cherenkov emissions from tissue being irradiated; and includes determining an actual applied dose map from the corrected images of Cherenkov emissions; and comparing the actual applied dose map to a planned dose map.

A method designated BF includes the method designated BE and further includes treating the lesion in the subject with radiation from a radiation beam source; and if the actual applied dose map differs from the planned dose map by more than a threshold, turning off the radiation beam source.

Changes may be made in the above system, methods or device without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system for monitoring a radiation treatment of a subject by generating and correcting images of Cherenkov emissions from a tissue of the subject comprising:
    a camera adapted to create images of Cherenkov emissions from the tissue of the subject, the Cherenkov emissions produced during the radiation treatment of the subject by an interaction of a treatment beam with the tissue of the subject;
    a source of three-dimensional voxel-based images of the tissue of the subject, selected from the group consisting of X-ray Computed Tomography (CT) images and Magnetic Resonance Imaging (MRI) images;

a processor adapted by a firmware in a memory to determine properties of a surface layer of the tissue of the subject from the three-dimensional voxel-based images of the tissue of the subject and determine optical Cherenkov correction factors (CF) compensating for a tissue attenuation therefrom using a correction factor determination method selected from the group consisting of:

calculating the optical Cherenkov correction factors based upon an electron density in the surface layer of the tissue of the subject as provided by the X-ray CT images, estimating a property map of surface layers of the tissue of the subject from the MRI images and calculating the optical Cherenkov correction factors therefrom, determining a tissue type map of the surface layers of the tissue of the subject, the tissue type map derived from the three-dimensional voxel-based images of the tissue of the subject, and determining the optical Cherenkov correction factors for a Cherenkov attenuation by a tissue type therefrom;

the processor configured to apply the optical Cherenkov correction factors (CF) to the images of Cherenkov emissions from the tissue of the subject to prepare Cherenkov images corrected for a Cherenkov light attenuation in the tissue of the subject.

2. The system of claim 1, wherein the surface layer of the tissue of the subject is sufficiently thick to include subsurface layers of the tissue of the subject from which Cherenkov emissions are emitted from the tissue of the subject, and is at least 5 millimeters (mm) thick.

3. The system of claim 2, wherein the correction factor determination method is selected from the group consisting of:

calculating the optical Cherenkov correction factors based upon an electron density in the surface layers of the tissue of the subject as provided by the X-ray CT images, and estimating a property map of the surface layers of the tissue of the subject from the MRI images and calculating the optical Cherenkov correction factors therefrom and wherein the camera is configured to obtain reflectance images of a surface of the subject, the processor is configured to determine second correction factors (CF2) therefrom and to apply the CF2 to the images of Cherenkov emissions from the tissue of the subject to generate corrected Cherenkov emissions images, the corrected Cherenkov emissions images corrected for a skin attenuation of the Cherenkov emissions from the tissue of the subject.

4. The system of claim 3, wherein the processor is configured to compare the corrected Cherenkov emissions images to a treatment plan of a dose delivery.

5. The system of claim 4, wherein the processor is configured to shut off a radiation source if the corrected Cherenkov emissions images differ from the treatment plan by more than a threshold.

6. The system of claim 2, wherein the correction factor determination method comprises determining a tissue type map of the surface layer of the tissue of the subject from the three-dimensional voxel-based images of the tissue of the subject of the subject and determining correction factors for the Cherenkov attenuation by the tissue type therefrom, and wherein the camera is also configured to obtain reflectance images of a surface of the subject, the processor is configured to determine second correction factors (CF2) therefrom and to apply the CF2 to the images of Cherenkov emissions from the tissue of the subject to generate corrected Cherenkov emissions images, the corrected Cherenkov emissions images being corrected for a skin attenuation of the Cherenkov emissions from the tissue of the subject.

7. The system of claim 1, wherein the correction factor determination method comprises calculating the optical Cherenkov correction factors from the electron density in the surface layer of the tissue of the subject as provided by the X-ray CT images.

8. The system of claim 1, wherein the correction factor determination method comprises estimating an electron density map of the surface layer of the tissue of the subject from the MRI images and calculating the optical Cherenkov correction factors from the electron density map.

9. The system of claim 1, wherein the correction factor determination method comprises determining a tissue type map of the surface layer of the tissue of the subject and determining the optical Cherenkov correction factors from the tissue type map.

10. A method of generating corrected images of Cherenkov emissions from a tissue exposed to radiation comprising:

making X-Ray computed tomography (CT) images or Magnetic Resonance Imaging (MRI) images of the tissue;

extracting a tissue surface volume from the X-Ray CT images or the MRI images;

determining correction factors CF in the tissue surface volume from the X-Ray CT images or the MRI images that correct images of Cherenkov emissions for a tissue absorbance;

obtaining images of Cherenkov emissions from the tissue as the tissue is exposed to radiation from a radiation beam source; and using the correction factors to correct the images of Cherenkov emissions.

11. The method of claim 10, further comprising obtaining reflectance images of a surface of the tissue, and using the reflectance images to further correct the images of Cherenkov emissions.

12. The method of claim 11, wherein the X-Ray CT images or the MRI images are X-Ray CT images and the correction factors are determined from a CT density by a calculation from the CT density.

13. The method of claim 11, wherein the X-Ray CT images or the MRI images are MM images and the correction factors are determined by using the MRI images to estimate an electron density map and a calculation from the electron density map.

14. The method of claim 11, wherein tissue types in the tissue surface volume are classified from the X-Ray CT images or the MM images to generate a tissue type map, and the correction factors are determined according to the tissue type map.

15. A method for monitoring a radiation treatment comprising:

using the method of claim 12 to generate corrected images of Cherenkov emissions from the tissue being irradiated;

determining an actual applied dose map from the corrected images of Cherenkov emissions; and comparing the actual applied dose map to a planned dose map.

16. A method for controlling a radiation treatment of a lesion in a subject comprising:
 determining a treatment plan for the lesion in the subject comprising a planned dose map;
 treating the lesion in the subject with radiation from a radiation beam source; using the method of claim 15 to verify an actual applied dose map corresponding to the planned dose map; and
 if the actual applied dose map differs from the planned dose map by more than a threshold, turning off the radiation beam source.

17. A method for monitoring a radiation treatment comprising:
 using the method of claim 13 to generate corrected images of Cherenkov emissions from the tissue being irradiated;
 determining an actual applied dose map from the corrected images of Cherenkov emissions; and
 comparing the actual applied dose map to a planned dose map.

18. A method for controlling a radiation treatment of a lesion in a subject comprising:
 determining a treatment plan for the lesion in the subject comprising a planned dose map;
 treating the lesion in the subject with radiation from a radiation beam source; using the method of claim 17 to verify an actual applied dose map corresponding to the planned dose map; and
 if the actual applied dose map differs from the planned dose map by more than a threshold, turning off the radiation beam source.

19. A method for monitoring a radiation treatment comprising:
 using the method of claim 14 to generate corrected images of Cherenkov emissions from the tissue being irradiated;
 determining an actual applied dose map from the corrected images of Cherenkov emissions; and
 comparing the actual applied dose map to a planned dose map.

20. A method for controlling a radiation treatment of a lesion in a subject comprising:
 determining a treatment plan for the lesion in the subject comprising a planned dose map;
 treating the lesion in the subject with radiation from a radiation beam source;
 using the method of claim 19 to verify an actual applied dose map corresponding to the planned dose map; and
 if the actual applied dose map differs from the planned dose map by more than a threshold, turning off the radiation beam source.

* * * * *